United States Patent [19]

Kolattukudy et al.

[11] Patent Number: 4,981,611

[45] Date of Patent: Jan. 1, 1991

[54] CUTINASE CLEANING COMPOSITIONS

[75] Inventors: Pappachan Kolattukudy, Columbus, Ohio; Ayrookaran J. Poulose, San Bruno, Calif.

[73] Assignee: Genencor, Inc., San Francisco, Calif.

[21] Appl. No.: 341,200

[22] PCT Filed: May 31, 1988

[86] PCT No.: PCT/US88/01844

§ 371 Date: Mar. 29, 1989

§ 102(e) Date: Mar. 29, 1989

[87] PCT Pub. No.: WO88/09367

PCT Pub. Date: Dec. 1, 1988

Related U.S. Application Data

[63] Continuation-in-part of Ser. No. 56,500, May 29, 1987, abandoned.

[51] Int. Cl.[5] .................. C11D 1/83; C11D 3/386

[52] U.S. Cl. ................. 252/550; 252/174.12; 252/174.21; 252/DIG. 12

[58] Field of Search .......... 252/174.12, DIG. 12, 252/550, 174.21

[56] References Cited

PUBLICATIONS

The Merck Index, Tenth Edition, 1983, p. 971.
Cutinases from Fungi and Pollen, P. E. Kolattukudy, pp. 1 and 486.

*Primary Examiner*—Dennis Albrecht
*Attorney, Agent, or Firm*—James G. Passé

[57] ABSTRACT

This invention relates to cleaning compositions and methods for using them. Particularly, the invention relates to compositions comprising a surfactant and a cutinase enzyme. A preferred cutinase is derived from *Pseudomonas putida* ATCC 53552. Excellent cleaning is obtained with a surfactant mixture containing sodium dodecyl sulfate and octoxynol.

1 Claim, No Drawings

CUTINASE CLEANING COMPOSITIONS

CROSS-REFERENCE TO RELATED APPLICATIONS

This application is derived from PCT Application Ser. No. PCT/US88/01844, filed on May 31, 1988 which, in turn, is a continuation-in-part of Ser. No. 07/056,500 and claims priority under 35 U.S.C. 120 from U.S. Ser. No. 07/056,500, filed May 29, 1987 and which is now abandoned.

BACKGROUND OF THE INVENTION (a) Field of the Invention

The invention relates to enzymatic cleaning compositions and methods for using them. Particularly the invention relates to cleaning compositions comprising a surfactant and a cutinase enzyme.

(b) Background Information

A wide variety of enzymes are well known for use in cleaning compositions. The use of *B. subtilisins* and *B. licheniformis* protease in commercial preparations is common. Other enzymes have also been used in commercial cleaning compositions such as, for example, U.S. Pat. No. 4,011,169, and British Patent No. 1,293,613. Also a comprehensive review article of lipases in cleaning compositions can be found in *Journal of Applied Biochemistry*, 2:218–229 (1980) in an article entitled "Lipases as Detergent Components". Lipolytic detergent additives are also known from e.g., British Patent Specification No. 1,293,613 and Canadian Patent No. 835,343.

U.S. Pat. No. 3,950,277 and British Patent Specification No. 1,442,418 disclose lipase enzymes combined with an activator and calcium and/or magnesium ions, respectively, which are utilized to pre-soak soiled fabrics and to remove triglyceride stains and soils from polyester or polyester/cotton fabric blends, respectively. Suitable microbial lipases for use therein (apart from animal and plant derived lipases) are said to be those derived from *Pseudomonas, Aspergillus, Pneumococcus, Staphylococcus,* and *Staphylococcus toxins, Mycobacterium tuberculosis, Mycotorula lipolytica,* and *Sclerotinia.*

British Patent Specification No. 1,372,034 discloses a detergent composition comprising a bacterial lipase produced by *Pseudomonas stutzeri* strain ATCC 19154. Furthermore, it is recommended that the preferred lipolytic enzymes should have a pH optimum between 6 and 10, and should be active in said range, preferably between 7 and 9. Around 1970, this presumed *Pseudomonas stutzeri* strain was reclassified as *Pseudomonas aeruginosa*, as appears for example from the ATCC catalogues.

European Patent Application EP-A-No. 0130064 discloses an enzymatic detergent additive comprising a lipase isolated from *Fusarium oxysporum* with an alleged higher lipolytic cleaning efficiency than conventional lipases.

In European Patent Application No. 0214761, enzymatic detergent additives are described as the active component including a microbially produced lipase from a strain of *Pseudomonas cepacia.* The lipases described therein are claimed to be superior to the lipolytic detergent action of the prior art, especially at low temperature washing processes (around 60° C. and below).

In PCT Patent Application No. 87/00859 other novel lipolytic enzymes are described as having an optimal pH in the range of 8–10.5 at a temperature of 60° C. or less from bacterial strains selected from *Pseudomonas pseudoalcaligenes, P. stutzeri* and *Acinetobacter calcoaceticus.* These enzymes are described as particularly effective at low temperatures; i.e., 40° C. or lower and effective in both liquid and solid detergent compositions.

Also in U.S. Pat. No. 3,950,277, it is described in general terms that lipases from Pseudomonas are suited as agents for removal of oily stains from fabrics, if used together with a special group of lipase activators. The art cited does not, however, cover cutinase enzymes from Pseudomonas or any other microbial source. However, prior art enzymes for use in cleaning compositions, while effective on many proteins and lipids, are not completely effective against all stains commonly found in laundry and other cleaning applications. Further, many lipases are not stable at pH 8–11 where most cleaning compositions are used. Even further, most enzymes for use in cleaning compositions are not very stable, if at all, under oxidative conditions or in the presence of other enzymes such as proteases.

SUMMARY OF THE INVENTION

Accordingly it has been discovered that combinations of a surfactant and a substantially pure microbial cutinase enzyme are effective compositions for cleaning applications. The cutinase enzyme preparations possess activity at pH of from about 8 and 11, exhibit cleaning activity in aqueous solution at concentrations from about 0.05 mg/L to about 100 mg/L or m ore at temperatures from about 20° C. to about 50° C.

The enzymes are oxidatively stable and stable in the presence of other enzymes such as proteases. Even further, the cutinases show a synergistic effect when a plurality of surfactants are used with the cutinase.

The invention also relates to the improved process for enzymatically cleaning a material with an aqueous solution; the improvement comprising adding a substantially pure cutinase to the cleaning solution.

DETAILED DESCRIPTION OF THE INVENTION

Applicants have discovered that cutinase enzymes are useful when included in cleaning compositions. These compositions may take on a variety of forms such as for laundry cleaning, household and industrial cleaning, and the like. The cleaning compositions comprise combinations of known surfactants and a microbial cutinase enzyme which can be used to clean a wide variety of materials. The composition can be added to aqueous solution or solid powder, or formulated in an aqueous solution or solid powder and used according to conventional cleaning techniques. In one embodiment, the surfactant employed in combination with the selected cutinase is compatible with the cutinase.

Enzyme

Cutinases are well known in the art and are available from a wide variety of sources. See Cutinases from Fungi and Pollen, P. E. Kolattukudy, pg. 472–504, incorporated herein by reference, for discussion of cutinases useful in the practice of the invention. A preferred cutinase is that cutinase isolated in a substantially pure form from *Pseudomonas putida,* particularly the P. putida, ATCC 53552, described in copending U.S. patent application, Ser. No. 932,959 filed No. 19, 1986 and incorporated herein by reference, which enzyme therefrom has the following amino acid sequence:

unpurified form but essentially free of other enzymes and enzyme sources.

The natural substrate of cutinase is cutin which is a

| 1 | | | | | | | | 10 | | |
|---|---|---|---|---|---|---|---|---|---|---|
| ala | pro | leu | pro | asp | thr | pro | gly | gly | pro | phe | pro |
| | | | | | | | 20 | | | |
| ala | val | ala | asn | phe | asp | arg | ser | gly | pro | tyr | thr |
| | | | | 30 | | | | | | |
| thr | ser | ser | gln | ser | glu | gly | pro | ser | cys | arg | ile |
| | | | 40 | | | | | | | |
| tyr | arg | pro | arg | asp | leu | gly | gln | gly | gly | val | arg |
| | 50 | | | | | | | | | 60 |
| his | pro | val | ile | leu | trp | gly | asn | gly | thr | gly | ala |
| | | | | | | | | | 70 | | |
| gly | pro | ser | thr | tyr | ala | gly | leu | leu | ser | his | trp |
| | | | | | | 80 | | | | |
| ala | ser | his | gly | phe | val | val | ala | ala | ala | glu | thr |
| | | | | | 90 | | | | | |
| ser | asn | ala | gly | thr | gly | arg | glu | ser | leu | ala | cys |
| | | | 100 | | | | | | | |
| leu | asp | tyr | leu | val | arg | glu | asn | asp | thr | pro | tyr |
| | 110 | | | | | | | | | 120 |
| gly | thr | tyr | ser | gly | lys | leu | asn | thr | gly | arg | val |
| | | | | | | | | 130 | | |
| gly | thr | ser | gly | his | ser | gln | gly | gly | gly | gly | ser |
| | | | | | | 140 | | | | |
| ile | met | ala | gly | gln | asp | thr | arg | val | arg | thr | thr |
| | | | | 150 | | | | | | |
| ala | pro | ile | gln | pro | tyr | thr | leu | gly | leu | gly | his |
| | | | 160 | | | | | | | |
| asp | ser | ala | ser | gln | arg | arg | gln | gln | gly | pro | met |
| | 170 | | | | | | | | | 180 |
| phe | leu | met | ser | gly | gly | gly | asp | thr | ile | ala | phe |
| | | | | | | | | 190 | | |
| pro | tyr | leu | asn | ala | gln | pro | val | tyr | arg | arg | ala |
| | | | | | | 200 | | | | |
| asn | val | pro | val | phe | trp | gly | glu | arg | arg | tyr | val |
| | | | | 210 | | | | | | |
| ser | his | phe | glu | pro | val | gly | ser | gly | gly | ala | tyr |
| | | | 220 | | | | | | | |
| arg | gly | pro | ser | thr | ala | trp | phe | arg | phe | gln | leu |
| | 230 | | | | | | | | | 240 |
| met | asp | asp | gln | asp | ala | arg | ala | thr | phe | tyr | gly |
| | | | | | | | | 250 | | |
| ala | gln | cys | ser | leu | cys | thr | ser | leu | leu | trp | |
| ser | val | gly | arg | arg | gly | leu | | | | | |

Other sources of bacterial and fungal cutinases include:
 Fusarium solani pisi
 Fusarium roseum sambucinum
 Fusarium roseum culmorum
 Helminthosporum sativum
 Ulocladium consortiale
 Streptomyces scabies
 Colletotrichum capsici
 Phytopthora cactorum
 Botrytis cineria
 Colletotrichum gloeosporioides The cutinase of the invention should preferably be selected to cause at least about 10%, and preferably 20%, hydrolysis of the given fat under given conditions. Normally the amount would be in a concentration of from about 0.01% to about 5.0% by weight of the surfactant, and preferably from about 0.05% to about 3%, such that upon dilution in wash water it is in a concentration of at least about 0.05 mg/L. Further, one skilled in the art could take the preferred cutinase or, for that matter, any cutinase of the invention or any immuniologically identical cutinase and use random or selective replacement of amino acids to produce other cutinases which are more or less selective toward given substrates or include modification in activity such as oxidative stability. Substantially pure cutinase includes the isolated enzyme as well as the broth containing the enzyme in unpurified form but essentially free of other enzymes and enzyme sources.

biopolyester polymer which covers the plant leaves, fruits, etc., see Structure, Biosynthesis and Biodegradation of Cutin and Suberin. (1981), P. E. Kolattukudy, Ann. Rev. Plant Physiol., 32, pgs. 539-567. Stains comprising lipids which could be hydrolyzed or bound by cutinase on a substrate such as cloth would be similar to the natural substrate cutin. Cutinase, for these types of stains, will be more effective than the prior art lipases. The cutinases will work especially well on gravy, oils and greases, plant or grass, oil based makeup and collar stains.

Cutiniases are distinguishable from other lipases by methods well known in the art, See R. E. Purdy and P. E. Kolattukudy, *Biochemistry*, "Cutinase Assay", 14:2831-2840, (1975). Microbial cutinases from both fungal and bacterial sources have very good activity at pH 8-pH 11 which is an ideal pH condition for detergent use.

Because of the specific activity of cutinases, it is a preferred aspect of the invention to combine one or more other cutinases, or one or more other enzymes, such as proteases, amylases or other lipases, along with the cutinase of the invention in the cleaning composition. Further, Applicant shows a synergistic increase in hydrolytic activity of cutinase when two or more surfactants are combined along with the cutinase enzyme.

Cutinases then are ideal for cleaning composition inclusion. They have stability oxidatively such as in H$_2$O$_2$. They have good stability in a temperature range of from about 20°–50° C. which is ideal from a cleaning point of view. They are also stable in the presence of other enzymes; e.g., proteases, and as such, are ideal for mixtures of enzymes.

The Surfactant

A number of known compounds are suitable surfactants useful in the present compositions. These include nonionic, anionic, cationic, or zwitterionic detergents, as disclosed in U.S. Pat. No. 4,404,128 to Barry J. Anderson and U.S. Pat. No. 4,261,868 to Jiri Hora et al. The art is familiar with the different formulations which can be used as cleaning compositions.

The Cleaning Compositions and Method of Use

Cutinases can be formulated as a purposefully added ingredient into known powdered and liquid detergents having pH between 6.5 and 12.0 at levels of about 0.01 to about 5% (preferably 0.05 to 0.5%) by weight of the detergent. These detergent cleaning compositions can also include other enzymes such as known proteases and amylases, as well as bleaches, colorants, builders, and stabilizers.

The cutinase of the invention may be added to powdered detergents in the form of granulates or prills, prepared by methods known in the art such as described in British Patent Nos. 1,324,166 and 1,362,365 and U.S. Pat. Nos. 3,519,570; 4,106,991 and 4,242,219.

The cutinase preparations of the invention can be prepared by cultivating the microorganisms defined herein or otherwise cutinase containing microorganism under appropriate conditions. In order to obtain reasonable yields of enzyme, media containing readily assimilable carbon and energy sources as necessary such as a nitrogen source, as well as calcium and magnesium salts and trace elements and cutin, or monomers of cutin, or compounds resembling cutin or cutin monomers. One could also obtain the gene for cutinan and express in any organism of choice where one may not have to add cutin or cutin monomers into the fermentation.

The addition of cutinase to conventional cleaning compositions does not create any special use limitation. In other words, any temperature and pH suitable for detergent compositions containing enzymes is also suitable for the present compositions.

Although the preferred form of the invention has been described above, it will be obvious to those skilled in the art to which the invention pertains, that, after understanding the invention and in view of the following testing as a whole, various changes and equivalent modifications may be made without parting from the scope of the invention as defined by the claims.

STABILITY CUTINASE AGAINST PROTEASES

Reaction conditions:
Buffer: 0.1 M NaP, pH 10
Temp: 37° C.
Lipase: 42 ug/ml
Approximately 1:1 protease:cutinase aqueous solution were made up with the following results.

ENZYME ACTIVITY

| Protease Incubation Time | 0 min | 5 min | 10 min | 15 min | 14 hrs |
|---|---|---|---|---|---|
| None | 1.57 | 1.60 | 1.47 | 1.63 | 1.61 |
| Maxacal (35 µg/ml) | 1.68 | 1.58 | 1.72 | 1.66 | 0.134 |
| Esperase (64 µg/ml) | 1.73 | 1.64 | 1.59 | 1.51 | 0.456 |

Maxical is Gist-Brocade's brand of subtilisin enzyme (protease) Esperase is Novo's brand of protease enzyme (protease)

TEMPERATURE STABILITY OF BACTERIAL CUTINASE

| HALF LIFE AT 50° C. | |
|---|---|
| pH | Hrs. |
| 7 | 30 |
| 8 | 25 |
| 9 | 12 |
| 10 | 0.3 |

Enzyme was incubated at 50° C. in 0.1M sodium phosphate buffer at various pH's and activity was measured by hydrolysis of trioctanoin in polyvinyl alcohol emulsions.

EFFECT OF DETERGENTS ON HYDROLASE ACTIVITY

Reaction Conditions
substrate: p-nitro-phenyl butyrate, 1 mm (pnp)
pH: 8.0
buffer: 0.1m tris pH 8.0
temperature: 25° C.
enzyme: bacterial cutinase from ATCC 53552

An aqueous solution with the following were made up and the enzyme activity was measured in these solutions using pnp as a substrate by following absorbance of p-nitrophenol at 410 mm.

| Triton x-100 (octoxynol) | SDS % (sodium dodecyl sulfate) | % Activity |
|---|---|---|
| 0 | 0 | 100 |
| 0.2 | — | 78 |
| 0.4 | — | 60 |
| — | 0.05 | 30 |
| — | 0.1 | 23 |
| — | 0.2 | 14 |
| — | 0.4 | 6 |
| 0.4 | 0.4 | 78 |
| 0.2 | 0.2 | 98 |
| 0.2 | 0.05 | 125 |
| 0.2 | 0.1 | 138 |
| 6.1 | 0.1 | 130 |
| 0.05 | 0.05 | 132 |

(1) Non-ionic detergent inhibition is not significant at low concentrations.
(2) An ionic detergent inhibitor at high concentrations.
(3) Mixture of anionic and non-ionic detergents stimulate activity.

STABILITY TOWARD OXIDANTS

Cutinase 0.5 mg/ml in 0/1m sodium phosphate buffer, was incubated with various levels of hydrogen peroxide at pH 8.4 and 25° C. for 2 hours, and hydrolytic activity was measured by a pH-stat using trioctanoim-polyvinyl alcohol emulsion.

| | Hydrolytic Activity |
|---|---|
| [$H_2O_2$ ppm] | % Remaining |
| 0 | 100 |
| 100 | 86 |
| 200 | 86 |
| 500 | 91 |
| 1000 | 95 |

TABLE 1

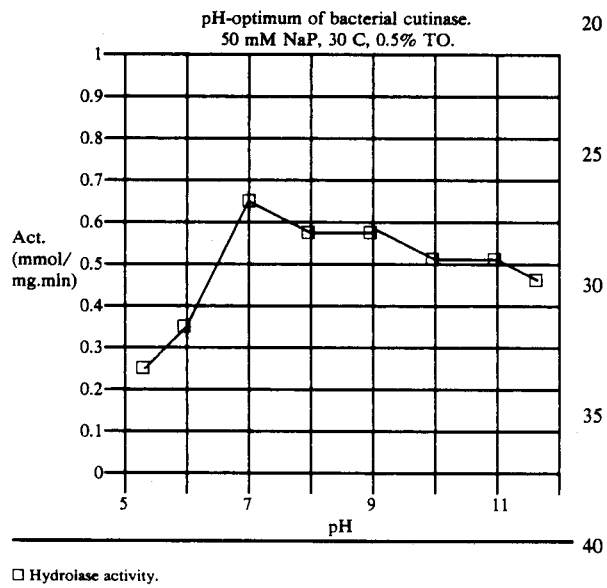

□ Hydrolase activity.

TABLE 2

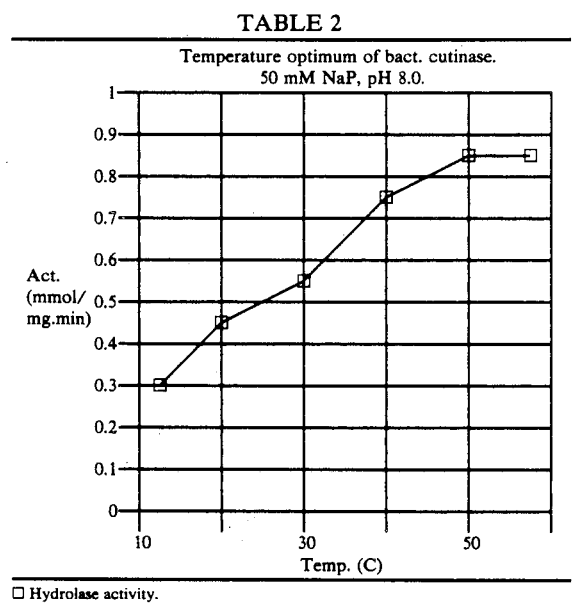

□ Hydrolase activity.

What is claimed is:

1. An improved method for enzymatically cleaning a material having a cutin stain comprising:
   (a) forming an aqueous solution comprising a cutinase enzyme derived from *Pseudomonas putida* ATCC 53552 having a concentration of said enzyme in said solution of from about 0.05 mg/l to about 100 mg/L, and a surfactant combination of sodium dodecyl sulfate and octoxynol wherein said sodium dodecyl sulfate is contained in said aqueous solution in a concentration of from about 0.05 to about 0.1 percent and further wherein said octoxynol is contained in said aqueous solution in a concentration of from about 0.05 to about 0.2 percent;
   (b) contacting the material to be cleaned with the aqueous solution of step (a); and
   (c) rinsing the material of step (b).

* * * * *

UNITED STATES PATENT AND TRADEMARK OFFICE
CERTIFICATE OF CORRECTION

PATENT NO. : 4,981,611

DATED : January 1, 1991

INVENTOR(S) : Pappachan Kolattukudy, Ayrookaran J. Poulose

It is certified that error appears in the above—identified patent and that said Letters Patent is hereby corrected as shown below:

Abstract, line 5, after "Pseudomonas" "putida" should be --mendocina--.

Column 2, line 67, after "Pseudomonas" "putida" should be --mendocina--.

Column 8, line 29, after "Pseudomonas" "putida" should be --mendocina--.

Signed and Sealed this

Thirty-first Day of March, 1992

Attest:

HARRY F. MANBECK, JR.

Attesting Officer      Commissioner of Patents and Trademarks